United States Patent
Anders et al.

[11] Patent Number: 5,997,815
[45] Date of Patent: Dec. 7, 1999

[54] ARTICLE WITH ANTIMICROBIAL COATING

[75] Inventors: Christine Anders, Haltern; Frank Hill, deceased, late of Mettmann, by Hella Luise Hill, Henning Hinrich Hill, legal representative; by Friedrich Frank Hill, legal representative, Waldsee; by Regina Luise Hill, legal representative, Speyer, all of Germany

[73] Assignee: Huels Aktiengesellschaft, Marl, Germany

[21] Appl. No.: 09/023,126

[22] Filed: Feb. 13, 1998

[30] Foreign Application Priority Data

Feb. 14, 1997 [DE] Germany ............... 197 05 579

[51] Int. Cl.⁶ ............... A61L 2/16; A61M 1/14; A01N 25/34
[52] U.S. Cl. ............... 422/35; 422/44; 422/45; 424/411; 424/423
[58] Field of Search ............... 422/28, 44, 45, 422/35; 424/411, 423, 429, 434, 435

[56] References Cited

U.S. PATENT DOCUMENTS 4,950,256  8/1990  Luther et al. .
5,217,493  6/1993  Raad et al. .
5,641,590  6/1997  Sato et al. ............... 429/192

FOREIGN PATENT DOCUMENTS 0 328 421   8/1989   European Pat. Off. .
36 27 316   2/1987   Germany .
40 40 363   6/1992   Germany .
3-244663   10/1991   Japan .
92/11081    7/1992   WIPO .

OTHER PUBLICATIONS

Patent Abstracts of Japan, vol. 016, No. 222 (P–1359), May 25, 1992, JP 04 045448, Feb. 14, 1992.

Donald A. Goldmann, et al., Clinical Microbiology Reviews, vol. 6, pp. 176–192, "Pathogenesis of Infections Related to Intravascular Catheterization", Apr. 1993.

*Primary Examiner*—Elizabeth McKane
*Attorney, Agent, or Firm*—Oblon, Spivak, McClelland, Maier & Neustadt, P.C.

[57] ABSTRACT

Articles that have an antimicrobial coating containing cyanoethylated hydroxyal-kylcellulose are provided, and their use in fields where preventing microbial contamination is important, such as in the medical field, where it is critical to minimize the spread of microbes that cause infection.

19 Claims, No Drawings

ARTICLE WITH ANTIMICROBIAL COATING

BACKGROUND OF THE INVENTION

1. Field of the Invention

The present invention relates to articles that have an antimicrobial coating.

2. Description of the Related Art

The ability of bacteria to colonize the surface of plastics, ceramics and metals is a serious problem in modern medicine. Articles implanted in patients, such as drainage tubes, stents, vascular prostheses, dental prostheses, cardiac valves, limb prostheses, contact lenses, artificial lenses and surgical suture materials, are prone to colonization by bacteria. Catheters, in particular, are preferred sites of colonization for bacteria (e.g. D A Goldmann and G B Pier, Clin. Microbiol. Rev. 6, 176192, 1993). When these articles act as a culture medium for antibiotic resistant bacteria, they put a patient at risk for developing an uncontrollable infection. Increasing numbers of antibiotic resistant bacteria have created an urgent need for articles nearly free of bacterial contamination (A G Gristina et al., Biomaterials, 8, 423426, 1987).

Several approaches have already been tried to prevent bacteria from colonizing on the surfaces of medical articles. Silver compounds (e.g. silver nitrate, silver zeolite and silver sulfadiazine) have been used as antibacterial agents in plastic catheters (EP 328 421, JA 03244663, J. Infectious Diseases 167, 920–924, 1992).

There have also been attempts to treat articles with high concentrations of antibiotics in order to prevent bacteria from colonizing on their surfaces. Antibiotics such as gentamycin, rifamycin, and ciprofloxacin have been used (J M Schierholz, Hospitalis 65, 403–407, 1995), as well as antiseptics such as biguanidines, iodine and/or chlorohexidine (G Golomb and A Shpigelman, J. Biomed. Mat. Res., 25, 937–952, 1991). For these compounds to be effective in preventing bacteria growth, they must be present at concentrations of 0.1 to 2% around the article surface. At these concentrations, the antibiotics and antiseptics will damage human tissues and cells. Moreover, when these articles come in contact with bodily fluids, the concentrations of antibiotics and antiseptics around the article surface will quickly drop below the level necessary for preventing bacterial growth. None of these approaches have shown promise in suppressing bacterial colonization on medical devices.

In addition to being susceptible to bacterial contamination, medical devices used as implants can cause dangerous blood clots. The clots are started when blood cells and other blood particles, such as thrombocytes, adhere to the surface of the implanted device. While certain disinfectants (e.g. benzalkonium chloride/heparin) have been shown to reduce the incidence of clotting, they have poor adherence to plastic, ceramic, and metal, and quickly dissolve off the surface of the implanted device.

Tissues can also adhere to an implant device, causing dangerous medical problems. For example, surgical procedures for inserting an intravascular catheter into a patient's blood vessel are complicated by the tendency of the vessel wall to grip the catheter surface. The resulting friction can cause a tear in the delicate inner lining of the vessel wall, and lead to the formation of a potentially deadly thrombus. Accordingly, the development of coatings that adhere to the surfaces of implantable medical devices, but not to blood cells and tissues, is an important goal for making safe implants.

Articles that can remain free from bacterial contamination would be useful in many applications in addition to medical devices. Pharmaceutical research with genetically engineered microbes, for example, requires large amounts of laboratory equipment to be exposed to experimental microbes. Savings in decontamination costs, as well as increased safety, would be realized if the equipment used in this research (e.g. containers, pipelines, bottles, pipettes, etc.) does not promote the growth of the contaminating microbes.

Cost could also be reduced by providing water treatment plants that resist bacterial growth. Presently, it is common for unchecked bacterial growth to clog and corrode waste water treatment plants. Plants that are built with equipment that can resist bacterial growth would last longer and require less maintenance. This equipment includes pipes, pumps, screens, and waste storage containers.

Sanitary conditions could also be enhanced by providing articles resistant to bacterial growth that are used to handle food and beverages. Also, the spreading of communicable disease would be reduced by providing bacterial resistant articles (e.g. seats, telephones, and toilets, doorknobs, handles, latches, etc.) in public places like airports, schools and hospitals.

SUMMARY OF THE INVENTION

Accordingly, one object of this invention is to provide novel articles that are nearly free from microorganisms. These articles also have low coefficients of friction, and are non-toxic to humans and animals. Another object of the invention provides a process of making these articles. A further object of the invention provides for using these articles in fields where it is important for articles to be nearly free of microbes.

These and other objects of the present invention have been satisfied by the discovery of a process for coating a substrate with cyanoethylated hydroxyalkylcellulose, the resulting coating article and its use in a variety of applications requiring anti-microbial surfaces.

DETAILED DESCRIPTION OF THE PREFERRED EMBODIMENT

Within the context of the present invention, articles that are "nearly free" from microbial contamination, means articles that have much fewer microbes on their surfaces (less than 50%, preferably less than 30%, more preferably less than 15% of the amount) than similar articles that do not have a cyanoethylated hydroxyalkylcellulose coating. Articles "nearly free" of microbial contamination thus also include articles that have no microbes on their surfaces. Moreover, microorganisms that are present on the surfaces of the articles of the present invention grow at much slower rates than they would on similar articles that do not have a cyanoethylated hydroxyalkylcellulose coating.

The terms "microorganism" and "microbe" have identical meanings in this application and should be interpreted to include a wide variety of cells and cell-like structures. Microorganisms include bacteria, yeasts, fungi, blood and tissue cells, and particles found in blood, such as thrombocytes.

The articles of the present invention are suitable for use in a wide variety of fields where antibacterial surfaces are required. They are useful in fields including food handling, hygiene, nutrition, pharmacology, and microbiology.

Articles of the invention useful for food handling include utensils, dishes, glasses, bowls, cutting surfaces, and counter tops.

Articles of the invention are especially useful for medical research and treatment. These articles include a wide variety of therapeutic and diagnostic medical devices, including catheters, stents, dialysis tubes, catheter tubes, drainage tubes, artificial blood vessels, cardiac valves, artificial limbs, dental prostheses, contact lenses, and surgical suture materials. The articles of the present invention also have particular use in pharmaceutical research and production where equipment, including containers, pipelines, packaging articles, and dispatch articles, must be nearly free of microbes.

Articles of the invention are also useful for articles that are handled by more than one person such as seats, telephones, and toilets, doorknobs, handles, and latches.

The articles according to the invention can be made from a wide variety of substrate materials: Metallic materials include iron, steel, stainless steel, nickel, titanium, manganese, and aluminum.

Ceramics include compositions of inorganic elements, such as nitrides, borides, carbides, suicides, oxides, and mixtures thereof Ceramics also include glasses, glass ceramics, oxide ceramics, and other partially crystalline inorganic materials.

Plastics include addition polymers, polycondensation products, and polyaddition compounds. Specific examples include polyolefins, such as polyethylene and polypropylene; copolymers of ethylene and propylene with one another and/or with other olefinically unsaturated monomers, such as 1-butene, vinyl acetate and acrylonitrile; polyesters, such as polyethylene terephthalate and polybutylene terephthalate; polycarbonates; polyamides, such as polycaprolactam and polylaurolactam; polyalkylene fluorides, such as polyvinylidene fluoride and polytetrafluoroethylene; and polyurethanes.

Articles of the present invention may also be made of a combination of the above mentioned metals, ceramics, and plastics.

Preparations and properties of cyanoalkylated hydroxyalkylcellulose have been described (J W Mays, Macromolecules 21, 3179–83, 1988 the content of which is hereby incorporated by reference). Coating compositions containing cyanoalkylated hydroxyalkylcellulose have also been described (DE Al-40 40 363 hereby incorporated by reference). This reference describes porous, compact substrates, including polyethylene film (Example 2), and microporous, polypropylene membranes for separating gas mixtures (Examples 7–9), having cyanoalkylated hydroxyalkylcellulose coatings.

The first step in making cyanoalkylated hydroxyalkylcellulose is the cyanoalkylation of hydroxyalkylcellulose. The hydroxyalkylcellulose should have a mean molecular weight of from 50,000 to 2,000,000, and can include commercially available hydroxyalkylcelluloses such as hydroxyethylcellulose and hydroxypropylcellulose. The product is dissolved in an inert solvent, such as tert-butanol, and an $\alpha,\beta$-unsaturated nitrile, preferably acrylonitrile, and a catalyst, are added to the solution. Typically, 0.1 to 3 mol of acrylonitrile is added to the solution per mole of glucose unit, or an excess of up to 5 times the equivalent amount, based on 3 reactive OH groups of the glucose unit. Examples of suitable catalysts are quaternary ammonium hydroxides, such as benzyltrimethylammonium hydroxide.

The articles according to the invention are made by coating a substrate with the cyanoalkylated hydroxyalkylcellulose. The coatings can be applied by any conventional coating technique such as dipping, spraying or spreading. Typically, the cyanoalkylated hydroxyalkylcellulose is dissolved in a volatile solvent, such as acetone, and coated onto the substrate. The solvent evaporates at, or slightly above, room temperature, leaving the cyanoalkylated hydroxyalkylcellulose coating on the substrate surface.

The resistance of the article to microbial growth is highest when the coating is completely smooth and pore-free. An smooth, pore-free coating is most easily produced when the underlying substrate is also smooth and pore-free. Articles with smooth, pore-free substrates are therefore preferred.

A cyanoalkylated hydroxyalkylcellulose coating is hydrophobic and insoluble in water, but it can absorb water and swell, depending on the degree of cyanoalkylation. The coating can be modified so it will no longer absorb water, and will no longer be soluble in organic solvents like acetone. This modification involves exposing the coated article to a plasma treatment or corona discharge, or to high-energy radiation. High-energy radiation is defined here to mean radiation more energetic than visible light, and includes UV rays, X-rays, and radiation generated by electron beams. The preferred method to modify the cyanoalkylated hydroxyalkylcellulose coating is to expose it to UV radiation.

The modified coatings have better adhesion to the underlying substrate than unmodified coatings, especially on smooth, pore-free substrates. The antimicrobial properties, the desired low coefficient of friction, and the low toxicity of the coatings are not diminished by their modification.

EXAMPLES

Having generally described this invention, a further understanding can be obtained by reference to certain specific examples that are provided herein for purposes of illustration only and are not intended to be limiting unless otherwise specified. All percentages are by weight, unless stated otherwise.

Example 1

Preparation of Cyanoethylated Hydroxypropylcellulose 0.03% of a benzyltrimethylammonium hydroxide catalyst was added to a 2.5% solution of hydroxypropylcellulose (molar weight about 1,000,000, Aldrich Chemie GmbH & Co. K G, Steinheim) in tert-butanol. Then a 5-fold molar excess of acrylonitrile per glucose unit with 3 hydroxyl groups was added dropwise. The mixture was warmed at 40° C. for 2 h and then concentrated under vacuum. The highly viscous solution was diluted with acetone, and mixed with an aqueous acetic acid solution, pH 3.5, that caused the cyanoethylated hydroxypropylcellulose to precipitate out of solution. The yield after reprecipitation was 60% of the theoretical yield, and the nitrogen content of the dried product was 3.7%, according to elemental analysis.

Example 2

Wettability of the Coatings Various plastics films were attached to a needle and immersed in a 1% acetonic solution of cyanoethylated hydroxypropylcellulose (AHC), according to Example 1. Excess solution was shaken off, and the film dried in air. A drop of water being applied to the film was recorded with a video camera. The image was digitized and the contact angle formed by the drop with the surface was measured.

TABLE 1

Wetting angles (degrees) of water on plastics films uncoated and coated with cyanoethylated hydroxypropylcellulose

| Film | uncoated | AHC 300/5 | AHC 5 million/5 |
| --- | --- | --- | --- |
| Polyamide 12 | 82.5 | 97 | 117 |
| Polyethylene | 96 | 87 | 113 |
| Polypropylene | 99 | 90 | 114 |
| Ethylene-vinyl acetate | 86 | 76 | 115 |
| Polyurethane | 89 | 87 | 121 |
| Polytetrafluoro-ethylene | 106 | 87 | 104 |

The values were the mean of 5 individual measurements.

The coatings did not make the plastic surfaces more hydrophilic. The product AHC 300/5 (hydroxypropylcellulose of molar weight 300,000 with 5 mol of acrylonitrile per mole of glucose unit) made the carrier film slightly hydrophilic, while the coating made from hydroxypropylcellulose of molar weight 1,000,000 made the plastic film slightly more hydrophobic.

Example 3

Bacterial Adhesion

Circular film sections of 1.6 cm in diameter were coated with AHC as in Example 2. Coated and uncoated films were shaken for 4 h in a suspension of living bacteria of the strain Klebsiella pneumoniae in phosphate-buffered saline (PBS), followed by washing twice with PBS. The adenosine triphosphate (ATP), present in the cells of the bacteria that adhere to the plastics film was extracted with boiling TRIS/EDTA buffer, and measured luminometrically with a reagent kit from Boehringer Mannheim. The measurement quantified the amount of bacteria adhering to the film in terms of light units (RLU). Table 2 shows difference in bacterial adhesion between coated and uncoated plastics.

TABLE 2

Change in bacterial adhesion to various plastics by coating with AHC (expressed in RLU × $10^{-3}$)

| Film | uncoated | AHC 300/5 | AHC 5 million/5 |
| --- | --- | --- | --- |
| Polyamide 12 | 64.5 | 15.7 | 18.1 |
| Polyethylene | 44.2 | 6.6 | 33.5 |
| Polypropylene | 50.5 | 30.1 | 10.0 |
| Ethylene-vinyl acetate | 26.2 | 14.7 | 5.3 |
| Polyurethane | 32.3 | 20.6 | 23.7 |
| Polytetrafluoro-ethylene | 126.0 | 37.8 | 24.4 |

A markedly reduced bacterial adhesion was found for all of the coated plastics.

Example 4

Thrombocyte Adhesion

Circular film sections of 0.8 cm in diameter are coated with AHC as in Example 2. Coated and uncoated film sections was shaken for 30 minutes in a citrate-containing rabbit blood, and then washed twice with PBS. The number of thrombocytes that remained on the film section was determined by a luminometry measurement of extracted ATP, similar to what was described in Example 3. Table 3 shows the relative number of adhering thrombocytes by way of the amount of ATP extracted from them, expressed in RLU.

TABLE 3

Change in thrombocyte adhesion to various plastics by coating with AHC (RLU × $10^{-3}$)

| Film | uncoated | AHC 300/5 | AHC 5 million/5 |
| --- | --- | --- | --- |
| Polyamide 12 | 424.3 | 6.0 | 26.1 |
| Polyethylene | 129.2 | 9.5 | 2.1 |
| Polypropylene | 155.1 | 3.7 | 5.1 |
| Ethylene-vinyl acetate | 159.0 | 65.2 | 5.9 |
| Polyurethane | 127.1 | 2.4 | 3.6 |
| Polytetrafluoro-ethylene | 170.8 | 5.6 | 9.3 |

Thrombocyte adhesion was reduced by up to 98% when the plastic film was coated with AHC. No hemolysis of the citrate blood by the coated or uncoated plastics was observed.

Example 5

Cytotoxicity

The cytotoxicity of coated films, relative to uncoated films, was determined by measuring changes in the growth rate of the ciliate *Tetrahymena pyriformis* exposed to the films. Inhibition of the growth of this ciliate has been used to measure the cytotoxic effect (DIN 13273, part 5, November 1986).

The films were sterilized by immersion in 70 percent by volume ethanol and then placed in a nutrient solution of 5 g proteose peptone, 4 g of peptone from casein, 1 g of meat extract and 200 mg of $K_2HPO_4$, per liter. The nutrient solution was then inoculated with *Tefrahymena pyrifonnis*.

The level of *Tetrahymena pyriformis* in the film containing nutrient solutions was determined by luminometry measurements of extracted ATP, similar to what was described in Example 3. These measurements revealed no differences in the cytotoxic effect of the AHC coated films compared to the uncoated films. In addition, a control film of flexible PVC with the preservative oxybisphenoxyarsine showed a pronounced cytotoxic effect.

Example 6

Coefficient of Friction

A catheter tube made of polyurethane (Pellethane®2363-90A) was immersed for 2 seconds in a 2% acetonic solution of cyanoalkylated hydroxypropylcellulose, dried overnight at room temperature, and heated at 40° C. for 1 h. The coefficient of friction of coated and uncoated catheter tubes was measured by moistening the tubes with distilled water and passing them through an appropriately sized loop. Table 4 shows the coefficient of friction for each tube.

TABLE 4

| Coating | Coefficient of friction |
| --- | --- |
| uncoated | 0.66 |
| AHC 1 million/5 | 0.34 |
| AHC 300/5 | 0.51 |

The coefficient of friction was reduced by coating with AHC.

Example 7

Solubility after Modification by UV Light

AHC coated films similar to those in Example 2 were irradiated with UV light (UV Excimer, Heraeus, type Exivac VAC; 1.7 kW) twice on each side for 1 minute each time, with 172 nm radiation, from a distance of 4 cm under vacuum at 1 mbar. The antimicrobial and thrombocyte-repellent properties of the coatings were not altered by the UV irradiation.

The solubility of the irradiated and nonirradiated coatings in acetone was tested by shaking a 5×7 cm film section weighing 220 mg in 10 ml of acetone for 10 minutes, drying in air, and weighing the coatings. The solubilities of the films in acetone are recorded in Table 5.

TABLE 5

Extraction of solids with acetone from coated and uncoated polypropylene (PP) films

| Film | UV irradiation | mg of extracted solids |
| --- | --- | --- |
| PP | − | 0.2 |
| PP | + | 0.4 |
| PP + AHC 300/5 | − | 7.7 |
| PP + AHC 300/5 | + | 0.6 |
| PP + AHC 1 million/5 | − | 6.9 |
| PP + AHC 1 million/5 | + | 0.4 |

The AHC coated films that were irradiated with UV light became almost insoluble in acetone.

The present application is based on German Priority Application 197 05 579.6, filed with the German Patent Office on Feb. 14, 1997, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. An article comprising:
    a substrate and a coating on said substrate, wherein said coating consists essentially of cyanoalkylated hydroxypropylcellulose, and
    wherein said substrate has a surface that is pore-free.

2. The article of claim 1, wherein said substrate is selected from the group consisting of metals, ceramics, and plastics.

3. The article of claim 1, wherein said substrate is selected from the group consisting of nitrides, borides, carbides, silicides, oxides, glasses, glass ceramics, and oxide ceramics.

4. A method of inhibiting microbial growth comprising:
    coating an article with a composition comprising an effective antimicrobial amount of cyanoalkylated hydroxypropylcellulose.

5. The method of claim 4, further comprising:
    crosslinking the coating on said article.

6. The method of claim 4, further comprising:
    exposing the coated article to plasma treatment, corona discharge, or high-energy radiation,
    wherein the high-energy radiation comprises radiation more energetic than visible light.

7. The method of claim 4, wherein said coated article comprises an amount of cyanoalkylated hydroxypropylcellulose needed to reduce the number of microbes on said coated article to less than 50% of the number of microbes present on an article that is identical with the exception that no cyanoalkylated hydroxypropylcellulose coating is present.

8. The method of claim 4, wherein said coated article comprises an amount of cyanoalkylated hydroxypropylcellulose needed to reduce the number of microbes on said coated article to less than 15% of the number of microbes present on an article that is identical with the exception that no cyanoalkylated hydroxypropylcellulose coating is present.

9. A method of inhibiting blood clots from forming on an article comprising:
    coating said article with a composition comprising an effective blood clot inhibiting amount of cyanoalkylated hydroxypropylcellulose.

10. The method of claim 9, further comprising:
    crosslinking the coating on said article.

11. The method of claim 9, further comprising:
    exposing the coated article to plasma treatment, corona discharge, or high-energy radiation,
    wherein the high-energy radiation comprises radiation more energetic than visible Light.

12. An article selected from the group consisting of biomedical articles, food handling articles, waste treatment articles, seats, telephones, toilets, doorknobs, handles, latches, containers, bottles, pipettes, pipes, pumps and waste storage containers, comprising:
    a substrate and a coating on said substrate, wherein said coating comprises cyanoalkylated hydroxypropylcellulose, and
    wherein said substrate has a surface that is pore-free.

13. The article of claim 12, wherein said biomedical article is selected from the group consisting of catheters, stents, dialysis tubes, catheter tubes, drainage tubes, artificial blood vessels, cardiac valves, artificial limbs, dental prostheses, contact lenses, and surgical suture material.

14. The article of claim 12, wherein said good handing article is selected from the group consisting of utensils, dishes, glasses, bowls, cutting surfaces, and counter tops.

15. The article of claim 12, wherein said substrate is selected from the group consisting of iron, steel, stainless steel, nickel, titanium, manganese, and aluminum.

16. The article of claim 12, wherein said substrate is selected from the group consisting of polyolefins, polyesters, polycarbonates, polyamides, polyalkylene fluorides, and polyurethanes.

17. The article of claim 12, wherein said coating comprises an amount of cyanoalkylated hydroxypropylcellulose needed to reduce the number of microbes on said coated article to less than 50% of the number of microbes present on an article that is identical with the exception that no cyanoalkylated hydroxypropylcellulose coating is present.

18. The article of claim 12, wherein said coating comprises an amount of cyanoalkylated hydroxypropylcellulose needed to reduce the number of microbes on said coated article to less than 15% of the number of microbes present on an article that is identical with the exception that no cyanoalkylated hydroxypropylcellulose coating is present.

19. The article of claim 12, wherein said coating comprises an effective blood clot inhibiting amount of cyanoalkylated hydroxypropylcellulose.

* * * * *